(12) United States Patent
Kasem (10) Patent No.: US 7,021,780 B2
(45) Date of Patent: Apr. 4, 2006

(54) TELESCOPIC MIRROR ATTACHMENT FOR MEDICAL, SURGICAL, AND DENTAL INSTRUMENTS

(76) Inventor: Raed S. Kasem, 3540 Florian Ter., Palm Harber, FL (US) 34685

( * ) Notice: Subject to any disclaimer, the term of this patent is extended or adjusted under 35 U.S.C. 154(b) by 0 days.

(21) Appl. No.: 10/201,927

(22) Filed: Jul. 25, 2002

(65) Prior Publication Data

US 2004/0017626 A1    Jan. 29, 2004

(51) Int. Cl.
*G02B 7/182*    (2006.01)
(52) U.S. Cl. ..................................................... 359/881
(58) Field of Classification Search ................ 359/881, 359/872, 875, 390, 385; 248/74.3; 433/29–31
See application file for complete search history.

(56) References Cited

U.S. PATENT DOCUMENTS

| | | | |
|---|---|---|---|
| 1,079,414 A | 11/1913 | Jirka | |
| 1,397,090 A | 11/1921 | Dimas | |
| 1,423,225 A * | 7/1922 | Knight | 359/881 |
| 1,509,041 A | 9/1924 | Hyams | |
| 2,258,126 A * | 10/1941 | Slutzky | 433/79 |
| 2,396,062 A * | 3/1946 | Tinnerman | 248/74.3 |
| 3,599,334 A | 8/1971 | Fuller | |
| 4,354,835 A | 10/1982 | Lewis | |
| 4,915,626 A | 4/1990 | Lemmey | |
| 5,027,138 A * | 6/1991 | Gandrud | 433/29 |
| 5,230,622 A | 7/1993 | Brossoit | |
| 5,458,486 A | 10/1995 | Ballard | |
| D379,656 S | 6/1997 | Reynolds | |

* cited by examiner

*Primary Examiner*—Euncha P. Cherry
(74) *Attorney, Agent, or Firm*—Berenato, White & Stavish LLC (57) ABSTRACT

A telescopic mirror attachment for use with medical, dental and surgical instruments to allow hands-free use of the mirror. The telescopic mirror attachment comprises a telescopic arm to which a mirror and a tightening grip are attached at either end by rotational connectors which allow axial and rotational positioning of the mirror relative to the medical, dental or surgical instrument. The tightening grip may be lined with an elastomeric or compressible material that provides further gripping.

53 Claims, 6 Drawing Sheets

TELESCOPIC MIRROR ATTACHMENT FOR MEDICAL, SURGICAL, AND DENTAL INSTRUMENTS

FIELD OF THE INVENTION

The present invention is directed to a telescopic mirror for attachment to medical, surgical, and dental instruments. The present invention more particularly relates to telescopic mirror attachment suitable for use with medical, dental, and surgical instruments such as a surgical microscope that does not require the operator to hold the telescopic mirror and its geometric arrangement provides for infinite adjustment.

BACKGROUND OF THE INVENTION

The use of a surgical microscope in medicine and dentistry improves the quality of patient care. The basic surgical microscope is an optical instrument, either mechanical, electrical or both, having a combination of lenses that provide the user with a stereoscopic, high quality magnified image of small structures within the surgical or treatment area. The use of the surgical microscope includes many medical and surgical disciplines and is also used extensively in dentistry. Many dental school teaching programs in the U.S. now require training on the microscope as part of their curriculum.

The surgical microscope is designed to allow the user to concentrate on the surgical procedure while remaining comfortable and free of eye-strain and also freeing both the user's hands to operate. Major advantages of using the surgical microscope are greater magnification and higher illumination of areas that could not be viewed or treated properly otherwise.

Microscopes are used either directly by positioning the magnifying lenses on top of the viewed object, or indirectly by using a hand held mirror that would reflect the object's image into the magnifying lenses. Indirect viewing under the microscope is widely used as it makes it easier to view an object in the human body that could not be viewed directly. An example of such viewing is the treatment of upper posterior teeth during endodontic or restorative dental procedures because in such treatment it is often impossible to have a direct view of the working areas without the use of a hand held reflective mirror.

However, the use of a hand held reflective mirror engenders its own set of problems and incurs other disadvantages. Among these disadvantages is the restriction of the user's ability to use both hands since one hand is occupied holding the mirror. This is of particular importance in performing delicate tasks where the use of two hands can be crucial. This also can lead to hand fatigue in that the use of one hand can lead to increased time for the procedure. Furthermore, continuous focus adjustment is needed during procedures using the microscope, thus forcing the user to continually interrupt the procedure to adjust and readjust the focus of the viewing area.

Attempts have been made to mount a dental mirror on the user's finger as shown in U.S. Pat. No. 5,458,486 to Ballard so as to permit finger manipulation of the mirror in the patient's mouth. However; even though the mirror is not hand-held, it still requires the use of one of the user's hands, thus resulting in all problems and deficiencies associated with the use of hand-held mirrors. Furthermore, the finger mounted mirror shown in U.S. Pat. No. 5,458,486 is not readily adjustable in use and does not have a wide range of adjustments.

Other attempts to attach a mirror to dental suction tips, for example, as shown in U.S. Pat. No. 5,230,622 to Brossoit, have also proven to have their own deficiencies. Although they do allow hands-free operation, the physical attachment to the suction tip limits the usefulness of the mirror as it cannot be positioned in a relatively stationary location in the mouth, but rather must follow with the dental suction tip. Furthermore, the clip on device does not allow a secure attachment that locks the mirror into place and does not permit dislodgement through use. Finally, the means of attachment to the dental suction tips greatly limits the range of motion and positionability of the mirror in the patient's mouth.

Also, mirrors need to be able to have their position readily and easily changed relative to the surgical microscope so as to permit the best possible view of the area and to allow sufficient illumination.

SUMMARY OF THE INVENTION

Accordingly, it has now been discovered that a telescopic mirror can be attached to the surgical microscope so as to free both of the user's hands. The telescopic mirror is securely attached so as to preclude dislodgement during the procedures, but is readily detachable to allow for sterilization of the mirror and to allow the telescopic mirror to be used with a variety of instruments and various types of surgical microscopes.

The telescopic mirror attachment of the present invention has an axial alignment that gives the mirror the ability to be infinitely adjustable relative to the surgical microscope, thus permitting optimal placement during any procedure.

The telescopic mirror device comprises a mirror portion that is connected to a telescopic arm by means of a flexible hinge that in a preferred embodiment is capable of 360 degree rotation. The telescopic arm allows adjustment of the distance of the mirror from the surgical microscope. The telescopic arm, in turn, is attached to a clamping or gripping device through a second flexible hinge so as to permit attachment to the surgical microscope or other medical, dental or surgical instrument. In a preferred embodiment, the second flexible hinge is also capable of 360 degree rotation.

An object of the invention is to permit hands-free use of a mirror that is capable of axial and rotational adjustment of the mirror relative to the medical, dental or surgical instrument being used in the procedure.

A further object of the invention is to provide a hands-free use of a mirror that can be selectively positioned and oriented relative to a surgical microscope or other medical, dental or surgical instrument so as to allow indirect viewing.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWING FIGURES

The accompanying drawings, which are incorporated in and constitute a part of the specification, illustrate presently preferred embodiments of the invention, and together with the general description given above and the detailed description of the preferred embodiments given below, serve to explain the principles of the invention. In the drawings.

DETAILED DESCRIPTION OF THE INVENTION

Respective embodiments of the present invention will be described hereinafter with reference to the drawings.

In the figures, identical parts bear identical reference characters; different parts having functions that are identical in principle bear identical reference characters with differing indices. The figures do not limit the invention, but rather are intended as possible exemplary embodiments.

The telescopic mirror attachment has a particular geometric arrangement in the form of an axial alignment that maximizes the degree of positioning of the mirror. The axial alignment of the telescoping arm in conjunction with the rotational connectors at each end of the telescoping arm allow the mirror to be adjusted in essentially an infinite number of positions. By movement simultaneously or individual movement of the telescoping arm and the two rotational connectors, the mirror can be adjusted to move, upward, downward, to the right, to the left, and rotate through a full 360 degree angle of rotation. Since the rotational connector connecting the mirror to the telescoping arm is a pivot point having a relatively short length as compared to the telescoping arm, it acts to provide a 360 rotational movement of the mirror relative to the telescoping arm centered at the connector. Likewise, the rotational connector connecting the securing grip to the telescoping arm is also a pivot point having a relatively short length as compared to the telescoping arm, and it also acts to provide a 360 rotational movement of the telescoping arm relative to the securing grip centered at the connector. The present invention allows for flexible movement in various angles so as to reduce restriction of viewing of the reflected objects. Thus, this arrangment acts to provide a stable but readily changeable mirror position relative to the surgical, medical, or dental instrument that maximizes flexibility in arrangment of the viewing field and minimizes any restrictions or obstructions in the field of view. This is achieved without patient discomfort associated with many prior art devices such as shown in U.S. Pat. No. 1,509,041 to Hyams; U.S. Pat. No. 4,354,835 to Lewis; and U.S. Pat. No. 1,397,090 to Dimas.

Figure 1:
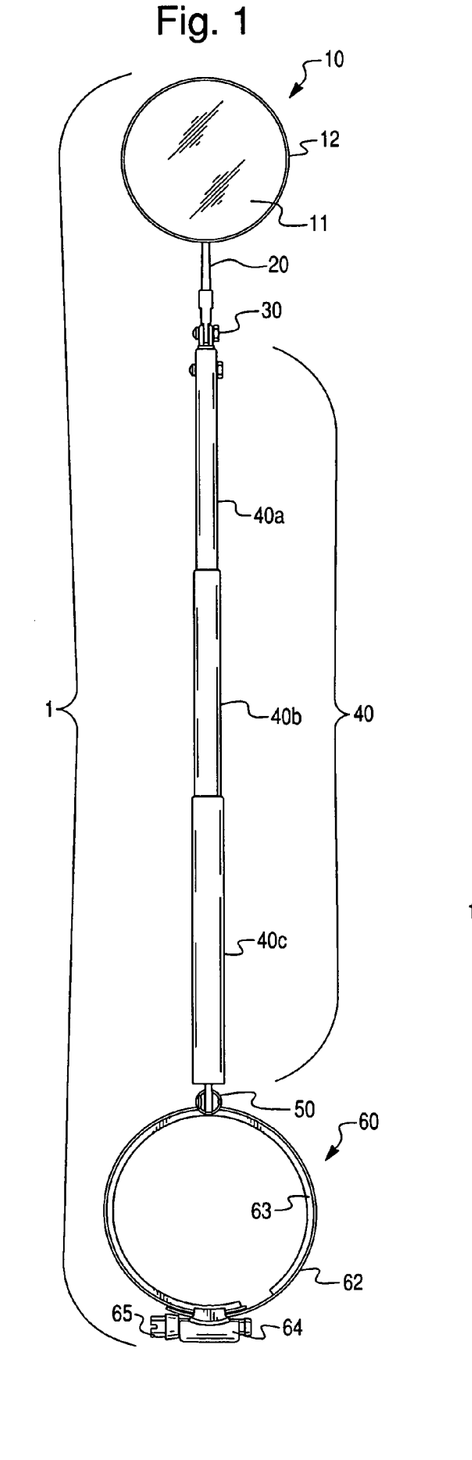
FIG. 1 is a top plane view of the telescopic mirror attachment of the present invention in its fully extended mode.
Figure 2:
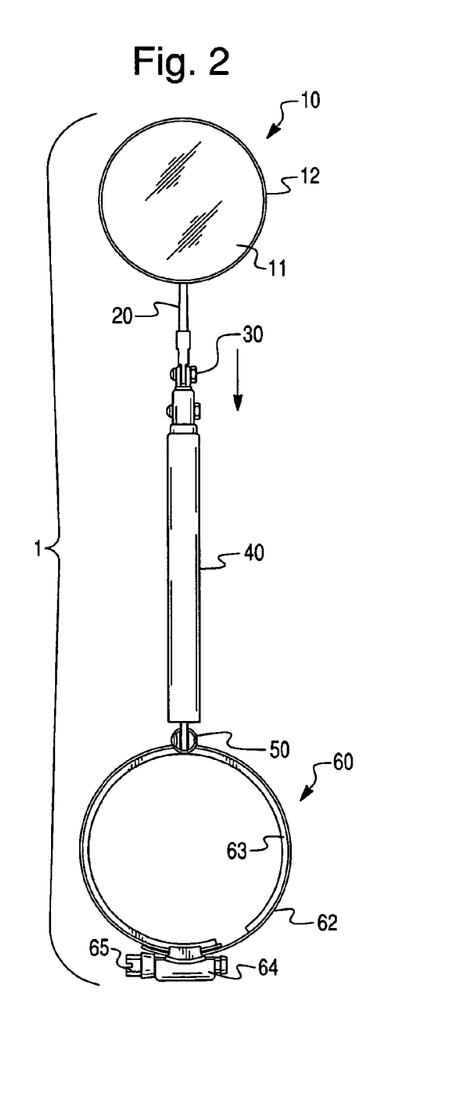
FIG. 2 is a top plane view of the telescopic mirror attachment of FIG. 1 in its fully collapsed mode.

The telescopic mirror attachment 1 of the present invention is shown in its fully extended mode in FIG. 1 and in its fully collapsed mode in FIG. 2. The telescopic mirror attachment 1 comprises a mirror 10, that may be a unitary structure or may consist of a mirror surface 11 in a holder or frame 12. The mirror 10 is attached to one end of a telescopic arm 40 through means of a rotational connector 30. In a preferred embodiment, an extension arm 20 is attached to the frame 12 of mirror 10 at one end and is attached to the rotational connector 30 at the other end. The other end of the telescopic arm 40 is attached to a tightening grip 60 by means of a second rotational connector 50. The tightening grip 60 is used to removably secure the telescopic mirror attachment 1 to the medical, dental or surgical instrument with which it is to be used.

Figure 3:
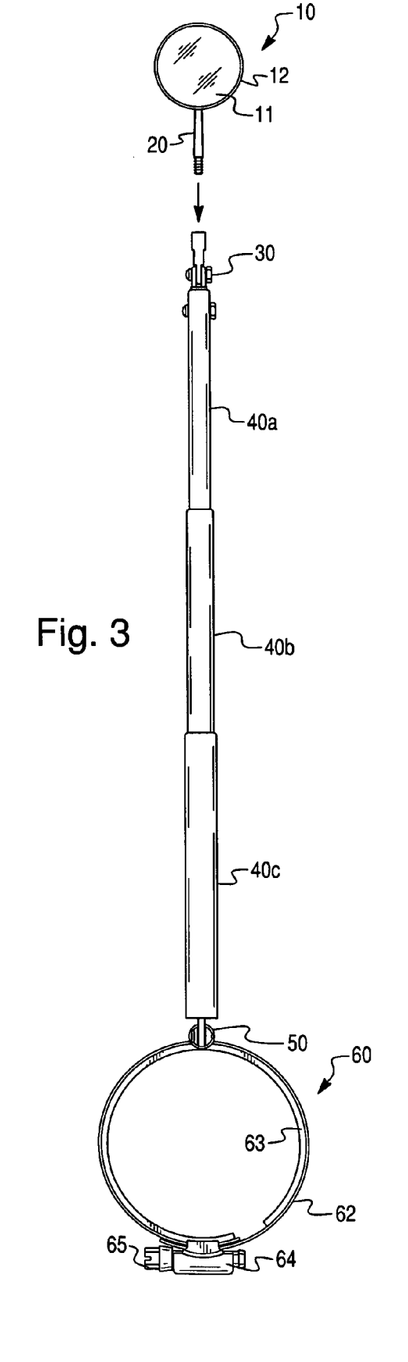
FIG. 3 is a top plane view of another embodiment of the telescopic mirror attachment of the present invention with a small mirror.
Figure 4:
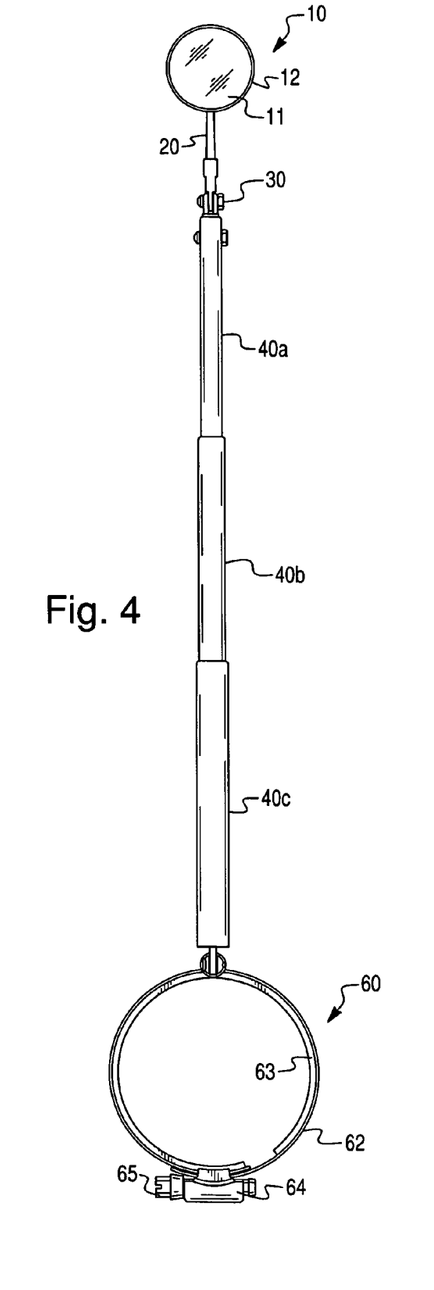
FIG. 4 is a side view of the telescopic mirror attachment of FIG. 1 in its fully extended mode.

The attachment of the extension arm 20, the telescopic arm 40 and the tightening grip 60 to the rotational connectors 30 and 50 can be by any suitable means known to one skilled in the art and can include screw threaded means such as shown in FIG. 3, quick release connector devices, and the like. The connection must be secure while in use, and is preferably suitable for a quick change, at least at the mirror end.

The mirror 10 is a conventional mirror of the type used in the medical, dental and surgical fields and is capable of being sterilized. The mirror can be provided as an autoclavable reusable item or may be provided as a sterile, disposable item. The mirror can be any suitable size or diameter for use as shown in FIGS. 1–4. Preferably, the mirrors suitable for use are interchangeable and can range in size and diameter. The mirror 10 can be replaced on the telescopic arm 40 during a procedure, for example, to provide a different magnification. The selection of suitable mirrors providing magnification would be known to one skilled in the art and would include mirrors that increase the magnification ratio through the microscope the desired amount such as 1:2 and 1:3, and greater. Although the microscope provides strong lighting, if additional lighting is required or desired it can be had through the provision of a lighted mirror.

The extension arm 20 is connected to the mirror 10, preferably by means of the mirror frame 12 by any suitable manner known to one of skill in the art such as by welding, gluing, soldering, epoxying, and the like. In an alternative embodiment of the present invention, the mirror frame 12 and the extension arm 20 are made as a single unit. In another embodiment, the connection between the mirror frame 12 and the extension arm 20 is flexible, thus permitting even greater articulation of the telescopic mirror attachment device 1.

The mirror and the extension arm are connected at the end of the extension arm to a rotational connector 30. In a further embodiment of the invention, the connector connecting the mirror 10 and extension arm 20 to the rotational connector 30 is of the quick release type known to those skilled in the art. In yet another embodiment of the invention, the connector connecting the mirror 10 and extension arm 20 to the rotational connector 30 is of a screw threaded type, as depicted in FIG. 3.

Figure 5:
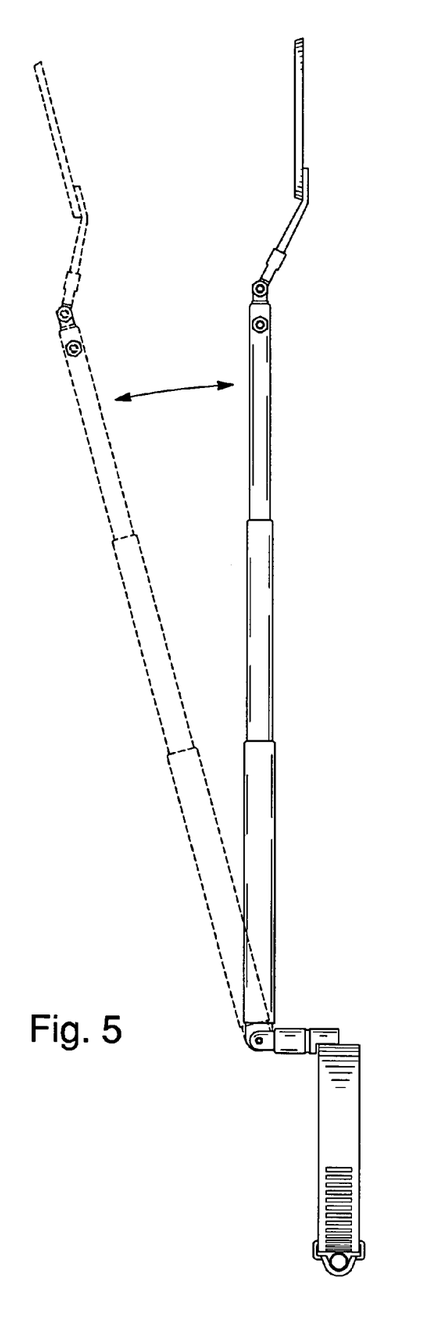
FIG. 5 is a side view of the telescopic mirror attachment of FIG. 1 showing pivoting at grip portion.
Figure 6:
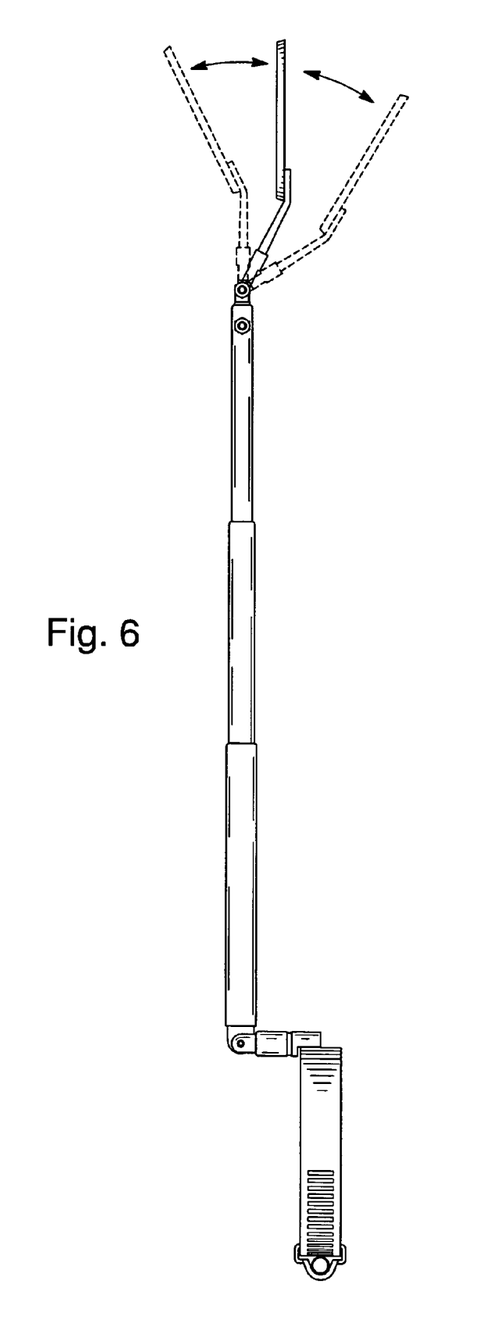
FIG. 6 is a side view of the telescopic mirror attachment of FIG. 1 showing pivoting at the mirror.
Figure 7:
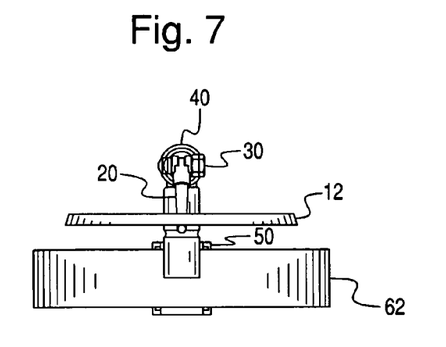
FIG. 7 is a top end view of the telescopic mirror attachment of FIG. 1.
Figure 8:
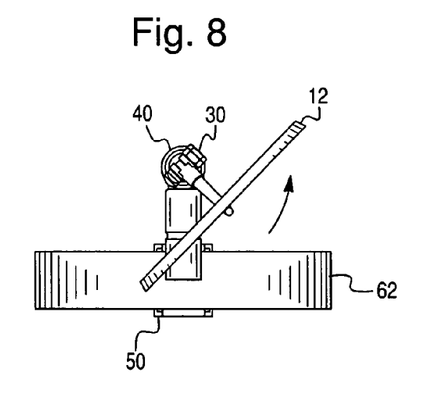
FIG. 8 is the top end view of the telescopic mirror attachment of FIG. 7 showing rotation at the mirror.
Figure 9:
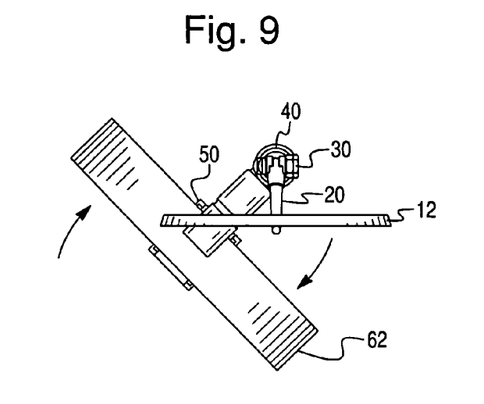
FIG. 9 is the top end view of the telescopic mirror attachment of FIG. 7 showing rotation at the grip portion.

As shown in FIGS. 5 through 9, rotational connectors 30 and 50 can be the same or different and can be any suitable device known to one of ordinary skill in the art. Suitable rotational connectors are capable of pivoting as shown in FIGS. 5 and 6, and/or rotating as shown in FIGS. 8 and 9 and include flexible hinges, ball-joints, and the like. In a preferred embodiment of the invention, the rotational connectors 30 and 50 are flexible hinges that can be both pivoted 360 degrees with the pivot point located at the end of the telescopic arm 40 and can be rotated about the telescopic arm 40 thus providing a rotation area of 360 degrees. In a further embodiment, the rotational connectors are sufficiently stiff so that they can be readily pivoted, but will normally hold their position during use.

The telescopic arm 40 consisting of telescoping arm segments 40*a*, 40*b* and 40*c* of the present invention allows the distance between the mirror 10 and the tightening grip 60 to be readily adjusted as shown in FIGS. 1 and 2. In a preferred embodiment, the telescoping mechanism of the telescopic arm 40 is sufficiently stiff so that the telescopic arm 40 can be readily lengthened (FIG. 1) or shortened (FIG. 2), but is capable of holding its position during use. In a preferred embodiment, the minimum length of the telescopic arm 40 (in its compressed position) is greater than the sum of the lengths of rotational connectors 30 and 50 and the length of extension arm 20. In a more preferred embodiment the minimum length of the telescopic arm 40 (in its compressed position) is at least two times the sum of the lengths of rotational connectors 30 and 50 and the length of extension arm 20. In another more preferred embodiment the minimum length of the telescopic arm 40 (in its compressed position) is at least three times the sum of the lengths of rotational connectors 30 and 50 and the length of extension arm 20. In a preferred embodiment, the expanded length of the telescopic arm is at least 75% greater than the compressed length, and more preferably double the compressed length. Telescoping arms that are capable of expanding to a multiple of the compressed length are also suitable for use in the present invention.

A particularly preferred telescoping arm is that similar to those of the antenna style design that is rigid enough to keep certain extensions fixed in a position securely during use, but can be readily changed as needed during use.

In one embodiment of the invention, the length of the telescopic arm 40 in the collapsed mode can range from about 1 to 10 inches, preferably about 4 inches; and the length of the telescopic arm 40 in the extended mode can range from 2 to about 40 inches, preferably about 12 inches. In a preferred embodiment of the invention, the length of the telescopic arm 40 can range from about 20 mm in the collapsed mode to about 60 mm and greater in the expanded mode.

In a further embodiment of the invention, the telescopic arm 40 can be locked into the desired length and unlocked as needed during use to adjust the length. Suitable locking mechanisms for use in the present invention are known to those skilled in the art.

Figure 10:
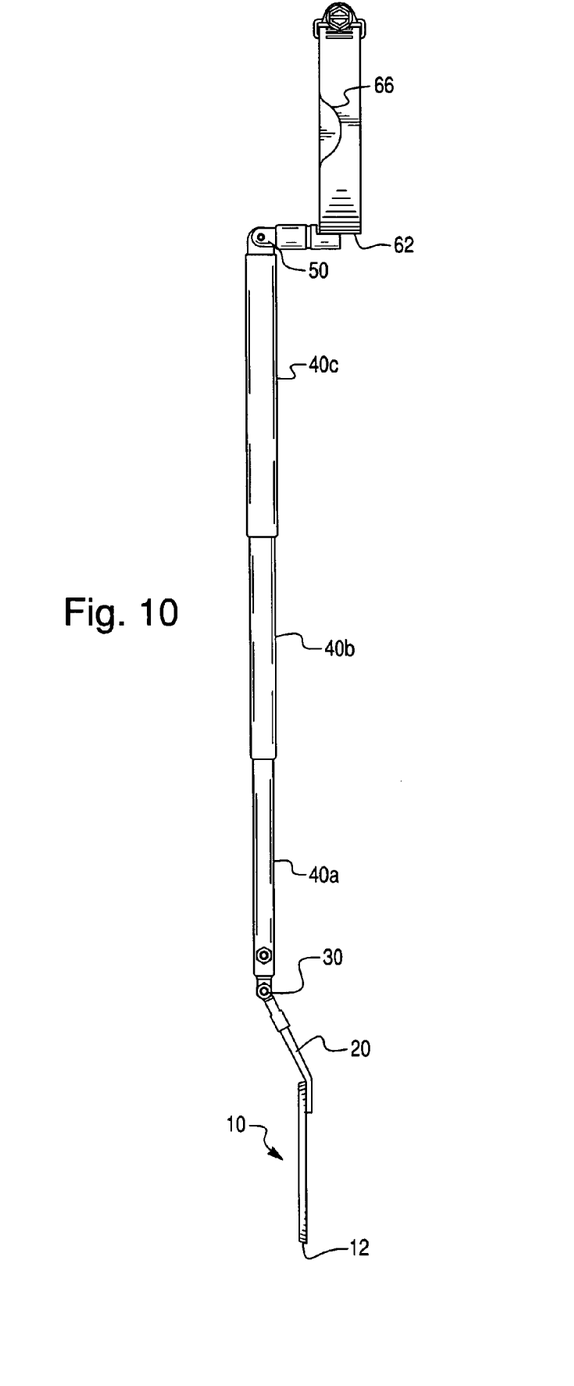
FIG. 10 is a side view showing another embodiment with a notch in the grip portion.
Figure 11:
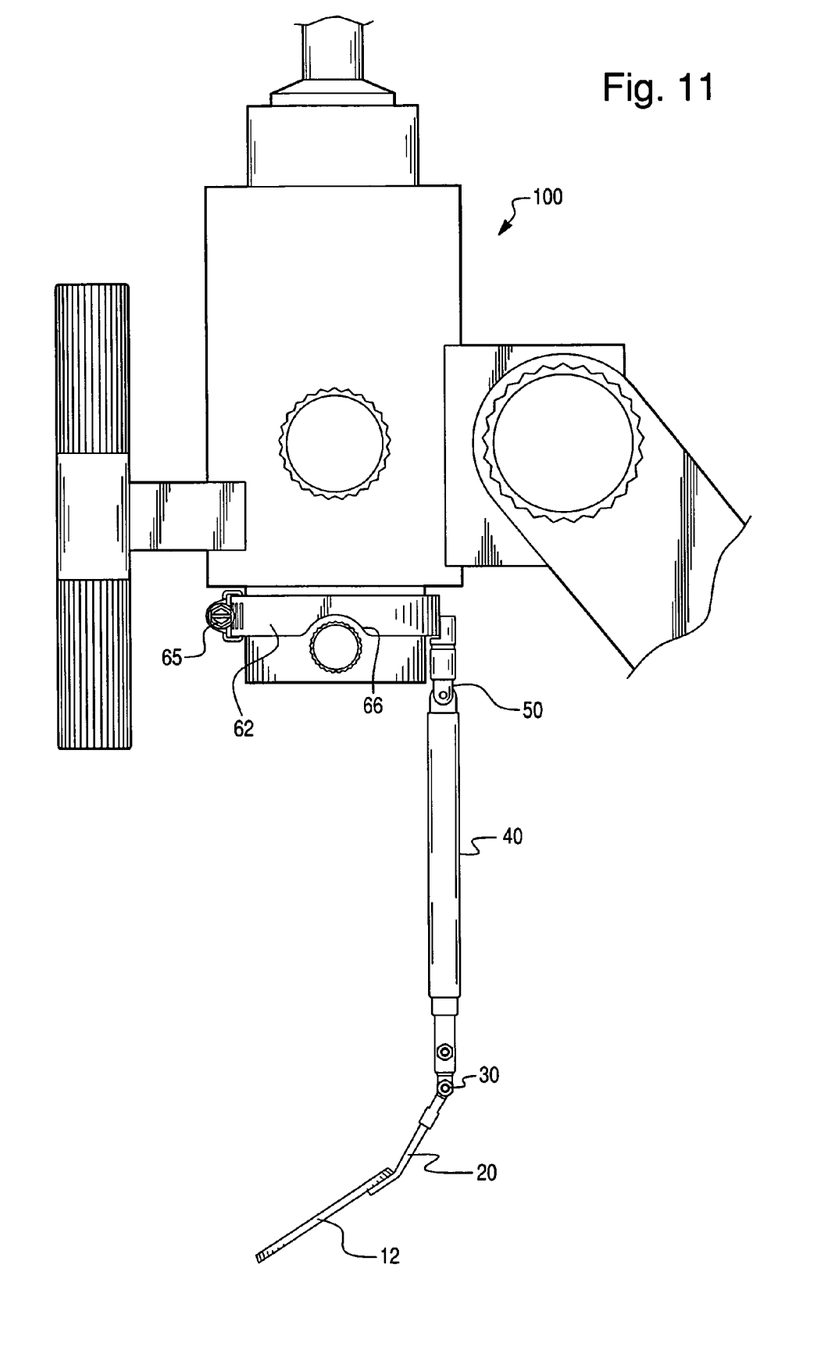
FIG. 11 is a side view of the telescopic mirror attachment of FIG. 1 attached to a surgical microscope.

Tightening grip 60 is used to removably attach the telescopic mirror attachment 1 to the medical, dental or surgical instrument with which it is to be used. In a preferred embodiment of the invention, the tightening grip 60 comprises an adjustable ring 62 that is capable of adjusting to a size sufficient to allow positioning over medical dental or surgical instrument. In a further embodiment of the invention, the adjustable ring 62 may contain cut portions 66 as shown in FIG. 10 that allow for the ring to fit more snugly against knobs and other projections on the surgical microscope or medical instrument as depicted in FIG. 11. For example, as shown in FIG. 11, the tightening grip 60 is attached to the lens of a surgical microscope 100. The tightening grip 60 can be also attached to the arm or other part of the microscope. In other embodiments, it can be attached to any suitable portion of the medical, dental or surgical instrument that will not adversely affect the procedure being undertaken, i.e. surgery, dental examination, endoscopic procedures, and the like. In yet other embodiments, it can be attached to a separate arm. Preferably the adjustable ring 62 is lined with a compressible material such as an elastomeric or cushioning material 63 that allows sufficient tightening of the adjustable ring 62 without damage or harm to the medical, dental or surgical instrument. In a preferred embodiment of the invention, the elastomeric or cushioning material 63 is of the type that enhances the gripping effect of the tightening grip 60, and would be known to one skilled in the art. Suitable materials include foam polymeric materials, rubber-type materials, velcro loop materials, and the like. In another embodiment, the elastomeric or cushioning material 63 is sterilizable, thus enabling the entire telescopic mirror attachment 1 to be sterilized or autoclaved between patients. The size of the tightening grip 60 is adjusted by means of a tightener 64 and tightening screw 65 working in cooperation to increase or decrease the size of the adjustable ring 62, so as to loosen or tighten the grip of the tightening grip 60.

As shown in FIG. 11, in operation, the telescopic mirror attachment 1 is removably attached to a medical, dental or surgical instrument, represented generically as 100. The tightening grip 60 is loosened by means of the tightener 64 and tightening screw 65 so as to increase the size of adjustable ring 62 sufficiently to slide it over the place where it is to be attached. In an alternative embodiment of the invention, the adjustable ring 62 can be loosened until it is opened, thus enabling it to be placed in locations where it is not possible to slide a ring over. The tightener 64 and tightening screw 65 are then tightened to decrease the size of the adjustable ring 62 so as to tighten it securely around the part it is to be fastened to. In a preferred embodiment of the invention, the adjustable ring 62 is tightened until the elastomeric or compressible material 63 is placed under sufficient compression to enhance the gripping effect of the tightening grip 60. When secured in this manner, the tightening grip 60 enables the telescopic mirror attachment 1 to be secured until it is desired to release the grip.

The practitioner then may adjust the telescopic arm 40 and the mirror 10 by adjusting the length of the telescopic arm 40 and by positioning of the rotational connectors 30 and 50 to achieve the best reflective image of the viewable area. The mirror can be adjusted to individually or simultaneously move upward, downward, right, left, and rotate 360 degrees. The mirror can then be adjusted, as needed, during the procedure so as to maintain the best reflective image of the viewable area or for the most advantageous viewing position. This adjustment can be made by any means comfortable to the practitioner and can include rotation at one or both of the rotational connectors 30 and 50, lengthening or shortening of the telescopic arm 40, or by simply grasping the mirror 10 and moving it into the desired position.

The mirror 10 of the telescopic mirror attachment 1 will remain in the selected position until readjusted as needed. This operates to free up both hands of the practitioner for use in the procedure.

In a further embodiment of the invention, the telescopic mirror attachment 1 is selectively removeable. The telescopic mirror attachment 1 can be removed after use and then either re-sterilized for use in another proceeding or is disposed of. The telescopic mirror attachment 1 can be replaced with a new or different telescopic mirror attachment 1 during a procedure as necessary; an example of a mirror attachment is a threaded screw type design.

Once given the above disclosure, many other features, modifications, and improvements will become apparent to the skilled artisan. Such other features, modifications, and improvements are, therefore, considered to be a part of this invention, the scope of which is to be determined by the following claims.

I claim:

1. A telescopic mirror attachment for attachment to a medical, dental or surgical instrument, said telescopic mirror attachment comprising:
   a mirror;
   a telescopic arm, said telescopic arm having a first end and a second end;
   a tightening grip capable of being removably attached to said medical, dental or surgical instrument;
   a first rotational connector connecting said mirror to said first end of said telescopic arm; and
   a second rotational connector connecting said second end of said telescopic arm to said tightening grip.

2. The telescopic mirror attachment of claim 1 further comprising an extension arm connecting said mirror to said first rotational connector.

3. The telescopic mirror attachment of claim 1 wherein said tightening grip comprises:
   an adjustable ring with an interior surface and an exterior surface;
   a compressible material lining said interior surface; and
   a tightening and loosening device for adjusting the size of the adjustable ring so as to tighten or loosen the grip of the tightening grip.

4. The telescopic mirror attachment of claim 1 wherein said mirror is removable.

5. The telescopic mirror attachment of claim 2 wherein the compressed length of the telescopic arm is greater than the sum of the lengths of both of said rotational connectors and said extension arm.

6. The telescopic mirror attachment of claim 2 wherein the compressed length of the telescopic arm is greater than twice the sum of the lengths of both of said rotational connectors and said extension arm.

7. The telescopic mirror attachment of claim 2 wherein the compressed length of the telescopic arm is greater than three times the sum of the lengths of both of said rotational connectors and said extension arm.

8. The telescopic mirror attachment of claim 1 wherein the expanded length of the telescopic arm is at least 75% greater than the compressed length of the telescopic arm.

9. The telescopic mirror attachment of claim 1 wherein the expanded length of the telescopic arm is at least twice the compressed length of the telescopic arm.

10. The telescopic mirror attachment of claim 1 wherein said rotational connectors are pivot points.

11. The telescopic mirror attachment of claim 1 wherein said telescopic mirror attachment is sterilizable.

12. The telescopic mirror attachment of claim 1 wherein said telescopic mirror attachment is disposable.

13. An infinitely positionable telescopic mirror assembly for secure, releasable attachment to a surgical, medical or dental instrument, said infinitely positionable telescopic mirror assembly comprising:
   a releasable securing grip for releasably securing said and assembly to said instrument;
   a mirror;
   a telescopic arm, having a central axis, a first end and a second end, wherein said telescopic arm can extend and contract, along said central axis;
   a first rotational connector, wherein said first rotational connector comprises a first pivot point; and
   a second rotational connector, wherein said second rotational connector comprises a second pivot point;
   wherein said first end of said telescopic arm is connected to said grip by said first rotational connector and said second end of said telescopic arm is connected to said mirror by said second rotational connector; wherein said assembly is adjustable by extension and contraction of said telescopic arm along its central axis, and by rotation of said first rotational connector and said second rotational connector.

14. The telescopic mirror attachment of claim 1, wherein said first rotational connector comprises a pivotal connector mechanism for pivoting said mirror relative to said telescopic arm and a rotational connector mechanism for rotating said mirror relative to said telescopic arm.

15. The telescopic mirror attachment of claim 14, wherein said second rotational connector comprises a pivotal connector mechanism for pivoting said tightening grip relative to said telescopic arm and a rotational connector mechanism for rotating said tightening grip relative to said telescopic arm.

16. The telescopic mirror attachment of claim 15, wherein:
   said pivotal and rotational connector mechanisms of said first rotational connector comprise separate structures from one another, and
   said pivotal and rotational connector mechanisms of said second rotational connector comprise separate structures from one another.

17. The telescopic mirror attachment of claim 1, wherein said second rotational connector comprises a pivotal connector mechanism for pivoting said tightening grip relative to said telescopic arm and a rotational connector mechanism for rotating said tightening grip relative to said telescopic arm.

18. The telescopic mirror attachment of claim 1, wherein said telescopic arm is extendable in length between about 4 inches and about 12 inches.

19. The infinitely positionable telescopic mirror assembly of claim 13, wherein said first rotational connector comprises a pivotal connector mechanism for pivoting said mirror relative to said telescopic arm and a rotational connector mechanism for rotating said mirror relative to said telescopic arm.

20. The infinitely positionable telescopic mirror assembly of claim 19, wherein said second rotational connector comprises a pivotal connector mechanism for pivoting said releasable securing grip relative to said telescopic arm and a rotational connector mechanism for rotating said releasable securing grip relative to said telescopic arm.

21. The infinitely positionable telescopic mirror assembly of claim 20, wherein:
   said pivotal and rotational connector mechanisms of said first rotational connector comprise separate structures from one another, and
   said pivotal and rotational connector mechanisms of said second rotational connector comprise separate structures from one another.

22. The infinitely positionable telescopic mirror assembly of claim 13, wherein said second rotational connector comprises a pivotal connector mechanism for pivoting said releasable securing grip relative to said telescopic arm and a rotational connector mechanism for rotating said releasable securing grip relative to said telescopic arm.

23. The infinitely positionable telescopic mirror assembly of claim 13, wherein said telescopic arm is extendable in length between about 4 inches and about 12 inches.

24. An assembly comprising:
a surgical microscope; and
a telescopic mirror attachment comprising a tightening grip capable of being removably attached to said surgical microscope, a mirror, a telescopic arm having a first end and a second end, a first rotational connector connecting said mirror to said first end of said telescopic arm, and a second rotational connector connecting said second end of said telescopic arm to said tightening grip.

25. The assembly of claim 24, wherein said first rotational connector comprises a pivotal connector mechanism for pivoting said mirror relative to said telescopic arm and a rotational connector mechanism for rotating said mirror relative to said telescopic arm.

26. The assembly of claim 25, wherein said second rotational connector comprises a pivotal connector mechanism for pivoting said tightening grip relative to said telescopic arm and a rotational connector mechanism for rotating said tightening grip relative to said telescopic arm.

27. The assembly of claim 26, wherein:
said pivotal and rotational connector mechanisms of said first rotational connector comprise separate structures from one another, and
said pivotal and rotational connector mechanisms of said second rotational connector comprise separate structures from one another.

28. The assembly of claim 24, wherein said second rotational connector comprises a pivotal connector mechanism for pivoting said tightening grip relative to said telescopic arm and a rotational connector mechanism for rotating said tightening grip relative to said telescopic arm.

29. The assembly of claim 24, wherein said telescopic arm is extendable in length between about 4 inches and about 12 inches.

30. An assembly for hands-free viewing of an object within a human body, comprising:
an instrument positioned outside of a human body and supported in a hands-free manner, the instrument selected from a medical, dental and surgical instrument;
a telescopic mirror attachment comprising a mirror, a telescopic arm having a first end and a second end, a tightening grip capable of being removably attached to the instrument, a first rotational connector connecting the mirror to the first end of the telescopic arm, and a second rotational connector connecting the second end of the telescopic arm to the tightening grip; and
wherein the first and second rotational connectors and the telescopic arm are manipulatable to position the mirror for viewing of an object in the human body while the instrument is maintained outside of the human body.

31. The assembly of claim 30, wherein the instrument comprises a surgical microscope.

32. The assembly of claim 30, wherein said first rotational connector comprises a pivotal connector mechanism for pivoting said mirror relative to said telescopic arm and a rotational connector mechanism for rotating said mirror relative to said telescopic arm.

33. The assembly of claim 32, wherein said second rotational connector comprises a pivotal connector mechanism for pivoting said tightening grip relative to said telescopic arm and a rotational connector mechanism for rotating said tightening grip relative to said telescopic arm.

34. The assembly of claim 33, wherein:
said pivotal and rotational connector mechanisms of said first rotational connector comprise separate structures from one another, and
said pivotal and rotational connector mechanisms of said second rotational connector comprise separate structures from one another.

35. The assembly of claim 30, wherein said second rotational connector comprises a pivotal connector mechanism for pivoting said tightening grip relative to said telescopic arm and a rotational connector mechanism for rotating said tightening grip relative to said telescopic arm.

36. The assembly of claim 30, wherein said telescopic arm is extendable in length between about 4 inches and about 12 inches.

37. A method for hands-free viewing of an object within a human body, comprising:
supporting an instrument outside of a human body in a hands-free manner, the instrument selected from a medical, dental and surgical instrument;
providing a telescopic mirror attachment comprising a mirror, a telescopic arm having a first end and a second end, a tightening grip capable of being removably attached to the instrument, a first rotational connector connecting the mirror to the first end of the telescopic arm, and a second rotational connector connecting the second end of the telescopic arm to the tightening grip;
attaching the tightening grip to the instrument; and
manipulating the first and second rotational connectors and the telescopic arm to position the mirror for viewing an object in the human body while maintaining the instrument outside of the human body.

38. The method of claim 37, wherein the instrument comprises a surgical microscope.

39. The method of claim 37, wherein the first rotational connector comprises a pivotal connector mechanism for pivoting the mirror relative to said telescopic arm and a rotational connector mechanism for rotating the mirror relative to the telescopic arm.

40. The method of claim 39, wherein the second rotational connector comprises a pivotal connector mechanism for pivoting said tightening grip relative to the telescopic arm and a rotational connector mechanism for rotating said tightening grip relative to the telescopic arm.

41. The method of claim 40, wherein:
the pivotal and rotational connector mechanisms of the first rotational connector comprise separate structures from one another, and
the pivotal and rotational connector mechanisms of the second rotational connector comprise separate structures from one another.

42. The method of claim 37, wherein the second rotational connector comprises a pivotal connector mechanism for pivoting the tightening grip relative to the telescopic arm and a rotational connector mechanism for rotating the tightening grip relative to the telescopic arm.

43. The method of claim 37, wherein the telescopic arm is extendable in length between about 4 inches and about 12 inches.

44. The telescopic mirror attachment of claim 2 wherein said extension arm is flexible.

45. The telescopic mirror attachment of claim 1 wherein said second rotational connector is connected directly to said tightening grip.

46. The infinitely positionable telescopic mirror assembly of claim 13 further comprising an extension arm connecting said mirror to said first rotational connector, wherein said extension arm is flexible.

47. The infinitely positionable telescopic mirror assembly of claim 13 wherein said second rotational connector is connected directly to said releasable securing grip.

48. The assembly of claim 24 wherein said telescopic mirror attachment comprises an extension arm connecting said mirror to said first rotational connector, and wherein said extension arm is flexible.

49. The assembly of claim 24 wherein said second rotational connector is connected directly to said tightening grip.

50. The assembly of claim 30 wherein said telescopic mirror attachment comprises an extension arm connecting said mirror to said first rotational connector, and wherein said extension arm is flexible.

51. The assembly of claim 30 wherein said second rotational connector is connected directly to said tightening grip.

52. The method of claim 37 further comprising an extension arm connecting said mirror to said first rotational connector, wherein said extension arm is flexible.

53. The method of claim 37 wherein said second rotational connector is connected directly to said tightening grip.

* * * * *